US009016940B2

(12) United States Patent
Fabrizio

(10) Patent No.: US 9,016,940 B2
(45) Date of Patent: Apr. 28, 2015

(54) MOBILE PATIENT POSITIONING CART FOR MULTIPLE EXPOSURE IMAGING EXAMS

(71) Applicant: Robert A. Fabrizio, Stamford, CT (US)

(72) Inventor: Robert A. Fabrizio, Stamford, CT (US)

(73) Assignee: Fujifilm Medical Systems U.S.A., Inc., Stamford, CT (US)

( * ) Notice: Subject to any disclaimer, the term of this patent is extended or adjusted under 35 U.S.C. 154(b) by 338 days.

(21) Appl. No.: 13/665,843

(22) Filed: Oct. 31, 2012

(65) Prior Publication Data

US 2013/0114790 A1    May 9, 2013

Related U.S. Application Data

(60) Provisional application No. 61/555,739, filed on Nov. 4, 2011.

(51) Int. Cl.
*A61B 6/04* (2006.01)
*G01N 23/04* (2006.01)
*A61B 6/02* (2006.01)
*A61B 6/08* (2006.01)
*A61B 6/00* (2006.01)

(52) U.S. Cl.
CPC ............... *A61B 6/02* (2013.01); *A61B 6/0492* (2013.01); *A61B 6/08* (2013.01); *A61B 6/4405* (2013.01); *A61B 6/4452* (2013.01); *A61B 6/447* (2013.01); *A61B 6/5241* (2013.01); *A61B 6/547* (2013.01); *A61B 6/587* (2013.01)

(58) Field of Classification Search
CPC ...................................................... A61B 6/0492
USPC ........................................................ 378/62, 177
See application file for complete search history.

(56) References Cited

U.S. PATENT DOCUMENTS

| | | | |
|---|---|---|---|
| 7,555,100 B2 | 6/2009 | Wang et al. | |
| 7,742,570 B2 * | 6/2010 | Yamaguchi | 378/98.12 |
| 2009/0238341 A1 | 9/2009 | Kawamura | |
| 2011/0038454 A1 | 2/2011 | Minnigh et al. | |
| 2011/0064193 A1 | 3/2011 | Minnigh et al. | |
| 2012/0059239 A1 | 3/2012 | Yamaguchi | |

\* cited by examiner

*Primary Examiner* — David J Makiya
*Assistant Examiner* — Danielle Fox
(74) *Attorney, Agent, or Firm* — Blakely, Sokoloff, Taylor & Zafman LLP

(57) ABSTRACT

A mobile patient positioning stand has a vertical rail allowing a shield structure to be moved up and down to different heights based on the height of anatomy of the patient desired to be imaged. The structure may be moved to position a shield of the structure at a height so that anatomy of a patient to be imaged is located within multiple image areas identified by markers on the shield. Then, an image detector holder and detector may be moved up and down to different heights behind the shield, based on the height of the markers. A source of radiation provides images at the multiple image areas. The multiple image areas may be connected by aligning stitching markers that may be on the shield, and are in the images. The aligning may be done by an automated computer software process that recognized patient anatomy and/or the stitching markers.

22 Claims, 4 Drawing Sheets

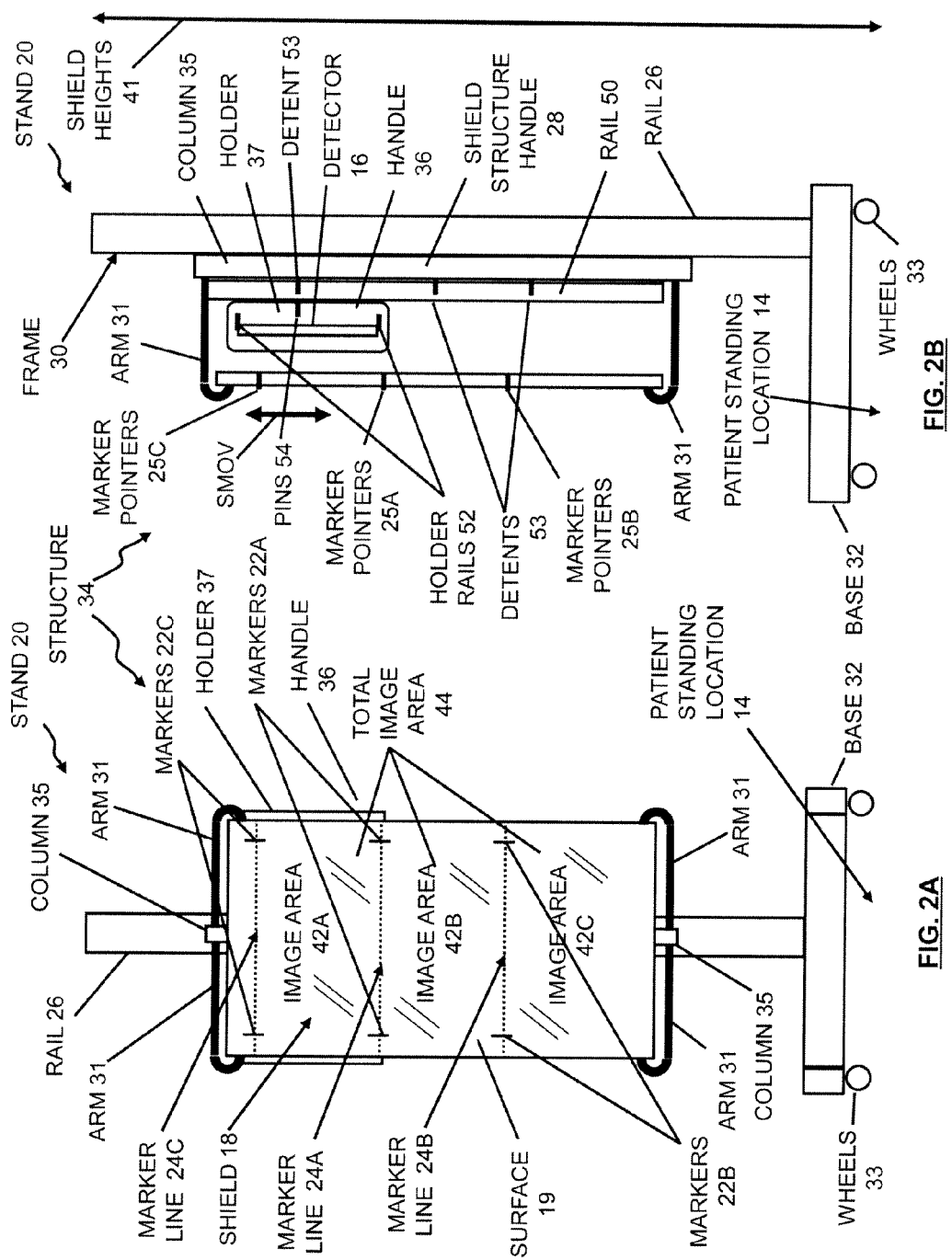

MOBILE PATIENT POSITIONING CART FOR MULTIPLE EXPOSURE IMAGING EXAMS

This is a non-provisional application claiming the benefit of U.S. Provisional Application No. 61/555,739, filed Nov. 4, 2011.

FIELD

Embodiments of the present invention relate to patient positioning shields for radiographic long length imaging, such as devices used to correctly mark borders of multiple images taken with a flat panel detector, so that the images can be properly aligned to form a longer length image area. Other embodiments are also described.

BACKGROUND

Medical radiographic imaging systems may apply radiation, such as x-rays, to a patient and detect radiation passing through the patient to obtain a radiographic image for diagnosis. In recent years, flat panel-type detectors have been used to detect a radiation image of a patient irradiated by a source (e.g., an x-ray tube). For some radiographic exams, multiple exposures may be needed to form an extended field of a long length image, due to the image detector having a smaller size than the long length image desired. Some types of desired exams associated with this type of extended field of view capture are exams such as: spine and scoliosis, long leg, and whole body imaging.

For example, traditional indirect forms of x-ray capture for such multiple captures may be achieved by overlapping multiples of analog x-ray film or re-useable computed radiography (CR) imaging plates, orienting them in one long length arrangement. Then a single exposure may be taken to expose all the capture areas at the same time. Resulting individual images can be processed separately (one at time) to transfer them to a processing workstation to be connected or stitched together.

In recent years, x-ray capture devices (e.g., detectors) have included portable electronic flat panel detectors which are directly connected (wired or wirelessly) to the workstation for immediate image transfer to the workstation (e.g., this provides "direct x-ray capture"). However, detectors may be significantly more expensive than film and it is less common to have multiple detectors. In addition, from the mechanical characteristics of their design it is not currently feasible to overlap them for a single long length exposure capture, since they consist of elaborate electronic components and surrounding structural hardware. Also an extended long sized (e.g., direct long length) detector may not be feasible for user versatility or cost.

This means that a long length capture requires separate multiple captures or images at sequential detector positions. Capturing multiple images separately introduces challenges in moving the detector behind the patient between each exposure. For example, upright x-ray exams are commonly performed using an upright or chest detector stand with some type of detector or image capture device inside. These upright devices feature the ability to position the detector at various heights depending on anatomy of interest and patient size. Some exams require multiple images at different heights to view a longer area of interest. It is preferable for these multiple images to be connected or "stitched" together as one extended length image.

SUMMARY

Embodiments of the invention provide improved systems, apparatus, and methods of use of a mobile patient positioning "cart" or stand for multiple exposure imaging exams. In some cases, such a cart may be described as "a mobile stitching cart" since it includes a mobile frame having a moveable patient positioning shield and detector holder (e.g., holding a detector) to be manually positioned at different heights based on the height of anatomy of the patient desired to be imaged, and based on a desired total image area (e.g., an image field) of a long length capture or image. A shield structure may be vertically positioned to position a shield at a height so that markers on the shield identify multiple image areas of desired images within the total image area desired for a certain height range of patient anatomy desired to be imaged. Multiple image areas may be needed due to use of an image detector of having a vertical size less than the desired total vertical image area size. After the shield is positioned as desired, a source of radiation may be vertically positioned to provide radiation for images at the multiple image areas within the total image area. A detector held by the detector holder may be manually positioned based on the vertical location of the markers on the shield, to provide the images at the multiple image areas. The vertical positioning may be determined by marker lines or pointer visible from the back of the shield. The multiple image areas may be identified in the images by the markers on the shield. After the images are generated, each image area may be connected to other image areas of the patient to form a total image area, such as a radiographic long length image.

FIGURES

The embodiments of the invention are illustrated by way of example and not by way of limitation in the figures of the accompanying drawings in which like references indicate similar elements.

FIG. 2A shows a front view of example embodiments of a portable patient positioning stand for multiple image areas of a total radiographic image area or field.

FIG. 2B shows a side view of example embodiments of a portable patient positioning stand for multiple image areas of a total radiographic image area or field.

Figure 3A:
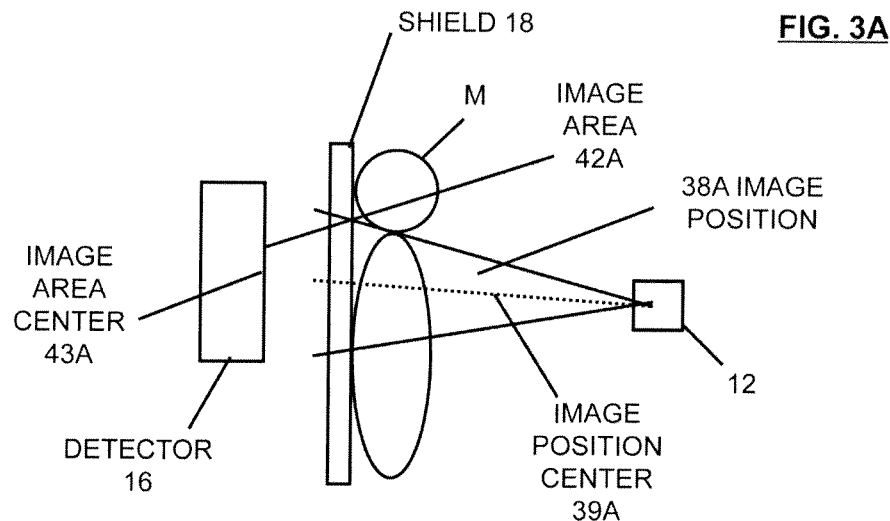
Figure 3B:
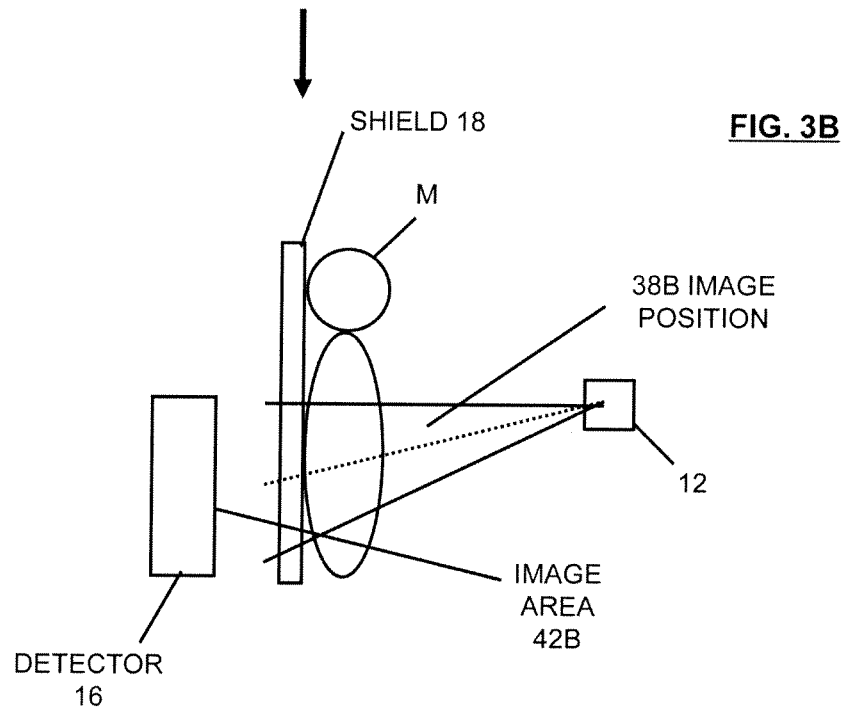

FIGS. 3A-B are side views illustrating example embodiments of a system for taking a long length of image of a spine using a portable patient positioning stand for defining multiple image areas of a total radiographic image area or field.

Figure 4:
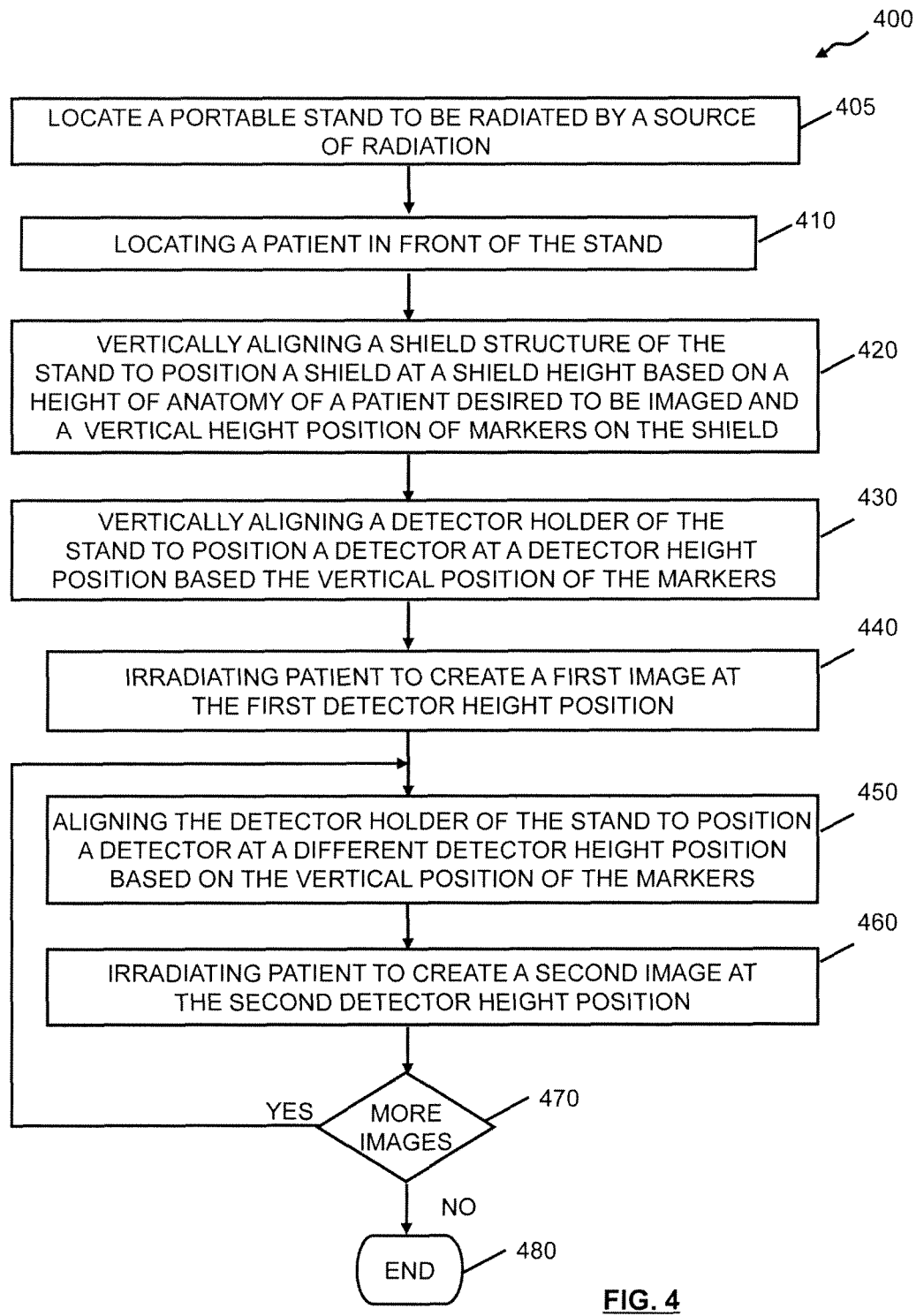

FIG. 4 shows example embodiments of a process for taking a long length of image of a spine using a portable patient positioning stand for defining multiple image areas of a total radiographic image area or field.

DETAILED DESCRIPTION

Several embodiments of the invention with reference to the appended drawings are now explained. Whenever the shapes, relative positions and other aspects of the parts described in the embodiments are not clearly defined, the scope of the invention is not limited only to the parts shown, which are meant merely for the purpose of illustration. Also, while numerous details are set forth, it is understood that some embodiments of the invention may be practiced without these details. In some instances, well known components or methods have not been described in detail in order to avoid unnecessarily obscuring the present invention. Similarly, in some instances, well-known circuits, structures, and techniques have not been shown in detail so as not to obscure the understanding of this description.

When using a radiographic detector smaller than a desired total vertical image height, a long length image may be obtained by connecting multiple images taken of image areas over a total image area. Markers or screen printed hair lines disposed on a shield between the patient and detector may provide marks for alignment of the images by being shown in the overlapping parts of the images together with the subject. The images may be connected or "stitched" together based on these markers being positioned at borders of image areas or frames. In some cases, the images can be aligned without markers simply based on a specified amount of image to image overlap (e.g., the height of image that exists in each image, beyond the markers). Thus, a portable patient "positioning stand" having a shield with the markers and or simple alignment lines may be used for multiple image exposures during imaging of a total image area, long length image or long length capture field.

Consequently, for these exams to work optimally, the patient should remain as still as possible for each capture exposure, so that anatomy in the image areas align well when stitched together. In these exams, it may be quite difficult for the technologist or user to accurately identify correct positions of the images (e.g., image areas), and amount of overlap of the images, when moving the detector to the next exposure position or location. If either of these are not accurate, the markers could miss the detector (e.g., not exist within the size of the detector) in one exposure or the other, or the amount of image overlap of adjacent images may not line up well enough for the software to automatically perform the stitching processing optimally.

Some patient positioning stands that exist for this type of purpose are designed primarily for a long length cassettes such as (14×34" or 14×50") used in CR (computed radiography), rather than for use with latest DR (direct radiography) flat panel detectors. Thus, these cassettes do not provide the improved imaging (e.g., increased resolution) of the latest DR (direct radiography) flat panel detectors. The latest DR detectors are currently only offered in traditional 14×17" or 17×17" sizes, which instead require multiple positions and exposures to capture a long length field size. Other stands are available for DR and CR. They offer patient position shielding from detector movements and are utilized in conjunction with automated detector positioning systems where the detector movement accuracy is determined by synchronized automated motorized positioning of the detector elevation and tube alignment. These stands do not provide usability for manually operated upright detector devices which are more common and less expensive. They also are not convenient for use in multiple rooms since they are typically specific to the upright stand they are built for. They also do not feature height adjustment of the glass shield, which assists in simplifying the alignment markers to the patient height. Some stands similar to this do not feature markings (e.g., marker lines or pointers) to align a manually operated detector system.

Embodiments of the invention are designed to perform multiple image captures for extended field of view exams utilizing a portable stand having a shield and a digital x-ray detector holder for use with a portable X-ray detector device or with traditional CR or analog film screen cassettes. Embodiments include a "portable" or "mobile" patient positioning stand designed for use with customer's existing upright chest digital capture device such as a flat panel detector or CR cassette combined with the associated computerized image processing workstation (and the source for providing the radiation for upright images). The portable stand includes a vertically moveable shield that helps steady the patient while multiple exposure exams are taken, such as to capture long view images. Typical digital x-ray workstations feature the ability to display, reprocess and send images to diagnostic workstations. In some embodiments, the alignment between vertically adjacent images is recognized by the capture workstation software by utilization of special shape lead makers. An "X" or "+" plus sign maker may be positioned on the right and left side of the outer edge of the area of the shield or screen (e.g., at a horizontal outer border of the shield) where the multiple images will be captured at an overlap to each other (e.g., at vertical borders between and included in adjacent images). The portable stand also includes a vertically moveable detector holder (and optionally a detector in place of or in the holder) that captures images based on or from received radiation while multiple exposure exams are taken, such as to capture separate long view images to be combined. Once the separate images are captured, the software looks for the markers and lines them up with the sequential images captured to accurately reproduce the overlap and align them together. Moreover, the cart or shield may be described as "universal" since it can be used with various imaging detectors, such as by including markings on the shield at different heights (or that are moveable to different heights) such that the markers will identify borders of image areas for various sized detectors and/or for detectors at different orientations.

Some embodiments of the invention provide a mobile frame having a shield that is movable (e.g., manually) on the stand and that has marker locations to simplify multiple detector positions for upright x-ray exams. The moveable shield is positioned in front of the detector "bucky" (e.g., detector holder), such as to hold a typical x-ray chest detector, to simplify and speed guidance of accurate position of the detector for each of the desired separate adjoining images. They may further conveniently adjust detector positioning markers to match desired field of view to patient height for proper detector anatomy height positioning, such as due to easy manual positioning of the shield height. The stand's shield may also shield the patient from detector movements hitting them. They may also help the patient remain steady and in proper position during the exam, by allowing patient to stand up against the shield, along with optional armrests which can further steady the patient. They may simplify detector alignment position accuracy for the multiple exams by use of lines or markers on the shield to quickly guide where the detector holder should be aligned for proper overlap amount for each exposure and may also include lines to help simplify alignment of the x-ray tube to the center of each capture area (e.g., image area) and may also simplify where the user can place special "moveable" stitching markers (optional) to accurately align with overlap areas of adjoining image/detector positions.

Some embodiments of the invention include a moveable (e.g., portable) stand, able to be used in any x-ray room, with any detector that fits its holder size (CR or DR). The stand may not require a separate holder for the detector such as a traditional chest stand devices. It may be designed to hold a detector (such as a flat panel DR detector or a CR or film-screen cassette). The stand may feature 2 primary independent movements to simplify the process of setting up for images based on the patient's specific height (or the height of anatomy desired to be imaged), which in turn accurately aligns detector positions between multiple exposures. A first independent movement may adjust the shield structure (with its detector holder) to the patient height, or adjust the shield structure height based on the height of the anatomy to be imaged. Then a second independent movement may provide a simple multi-position adjustment for the location of the detector behind the shield, for each exposure. Setting the patient height aligns (or adjusting the shield structure height based on the height of the anatomy to be imaged) the detector holder to patient height, then the secondary movement can have fixed precise detent positions to allow movement to the exact measured positions of a detector holder, as required for accurate overlap of the images based on the type of detector device, its size and its field of active capture area.

In some cases, the detector holder may be described as a "universal" holder since it is able to hold various sized detectors and hold detectors at different orientations (e.g., wider or taller, such as a 14 inch by 17 inch detector). Moreover, the stand may be described as a "portable and universal" stand since it may include marking on the shield at different heights (or that are moveable to different heights) such that the markers will identify borders of image areas for the various sized detectors and/or for detectors at different orientations.

Figure 1:
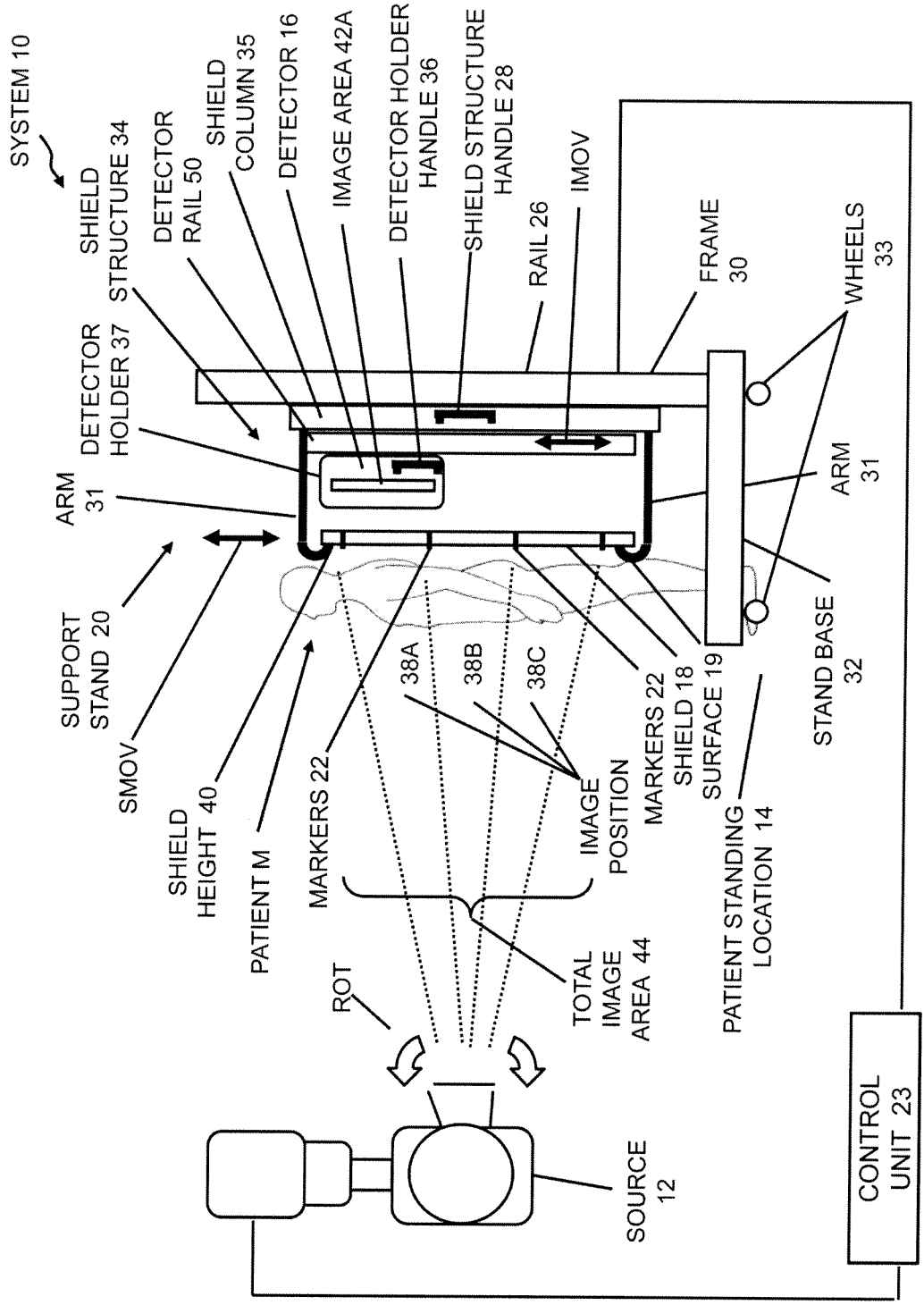
FIG. 1 shows example embodiments of a patient positioning system for multiple image areas of a total radiographic image area or field.

FIG. 1 shows example embodiments of a portable patient positioning system for multiple image areas of a total radiographic image area or field, such as of a desired long length image. In FIG. 1, system 10 is shown including radiation (e.g., x-ray) source 12 to irradiate patient M, standing at patient standing location 14 of patient positioning stand 20, to form an image using image detector 16 held by detector holder 37. Detector holder may be able to hold any of various traditional chest imaging detector devices and shield 18 may be positioned, close to without touching, just in front of the detector holder. System 10 includes stand 20 with manually movable shield 18 having x-ray transparent (not radiographic imagable markings or markers 22, such as markings on front or outer or rear surface 19 (or adhered directly to the front of the detector), such as for identifying or marking borders of adjoining radiographic image areas (e.g., areas 42A-C) of total image area or field 44. In some cases, each image area 42A, B and C may correspond to an image position of source 12 and detector 16, such as during x-ray exposure imaging or exams. Total image field 44 is longer than a length of any single one of image areas 42A-C, and each image area of areas 42A-C corresponds to one of image positions 38A-C of field 44. Positions 38A-C may correspond to a height of shield 18, detector holder 37 and/or of detector 16. In some cases, positions 38A-C may be selected by moving detector 16 to a height position for imaging image area 42A-C (e.g., as identified by markers 22), and then rotating the angle of the radiation output of source 12 along vertical rotational direction ROT to a proper centering to irradiate each image area (e.g., source 12 rotates around a horizontal axis going into the page of FIG. 1). Positioning the radiation output of source 12 could also be achieved by vertical up or down movement of the x-ray source (e.g., with or without rotation ROT), however rotation may be preferred for optimal imaging. Source (12) position could also be achieved by vertical up or down movement of the x-ray source (12), however rotation may be preferred for optimal imaging. Markings or hash marks on the stand shield or edges may be included (such as markers 22, lines 24 or pointers 25) to help simplify accurate centering of x-ray source with each image field by using the x-ray source's centering laser and or collimation light field. Each image area may correspond to or represent an image of patient M to be connected to at least one other image of the patient (corresponding to an adjacent image area) to form total image area 44. Source 12 may rotate to positions in a range between the minimum and maximum height of detector holder 37. In some embodiments, source 12 may be an x-ray source, such as a radiation source for imaging as known in the art. In some cases, source 12 may be a source for traditional CR or analog film screen cassette imaging x-ray system, as known in the art.

Stand 20 is shown including frame 30 having vertical stand rail 26 and base 32 below and attached to the rail. The base may have wheels. In some cases the base has arms with wheels 33 for rolling on a floor (or no wheels). Thus, stand 20 may be moved across a floor of rooms and down hallways, such as to be moved to and used in different rooms of a medical facility.

Shield structure 34 (e.g., a "frame" holding a shield and detector holder) is shown having shield column 35 movably coupled to stand rail 36 (or may be directly slidably mounted on the rail, or similar) to be manually moved vertically along the stand rail. Shield structure 34 has arms 31 to hold shield 18 at a fixed height with respect to the shield column. Arms 31 may be two or more arms to hold the shield at a relatively fixed location and height with respect to column 35. In some cases there are 4 arms (e.g., see FIGS. 2A-B). Thus, shield structure 34 (and shield 18) may be manually moved in vertical directions SMOV to position shield 18 at shield height 40 (e.g., vertically moveable) to provide one or more type of markers at positions on the shield. These markers may be x-ray transparent markings (e.g., do not show in captured images, such as lines 24) for identifying accurate detector alignment positions, such as at borders of image areas 42A-C, between source 12 and detector 16; and for identifying center of overlap areas for placement of processing software identifiable makers (x-ray image able markers), such as markers 22) and center markings (not shown) for tube laser alignment to the center of each image areas 42A-C. Marker positions along lines 24A & B in images of image areas 42A-C can be used for accurately connecting (e.g., overlapping or stitching) the images, such as based on the image identifiable marker positions within the overlap are of each adjoining image.

Shield 18 may include a flat or planar shield of a radio transparent material. In some embodiments, the material may be glass, polycarbonate glass, plexiglass, or another material as know in art. Markers 22 may be or include "stitching markers" as known in the art. Markers 22 may be or include a material having a large enough radiographic attenuation (e.g., a large enough radiation attenuation or absorption coefficient) to be radiographic imagable or recognizable by software in a radiographic image. The shield material may be visually transparent; bound in fiber, plastic and/or wood, and transparent to x-rays. The shield may have planar front surface 19 having markings 24 and markers 22, and a parallel planar back surface. Markers 22 may be or include "stitching markers" as known in the art. Markers 22 may be attached to or formed on surface 19 of the shield, such as on the front surface of the shield. In some cases, markers 22 may be attached to or formed on back surfaces of the shield. Markers 22 may be or include a material having a large enough radiographic attenuation to be radiographic imagable or recognizable by software in a radiographic image. Markers 22 may be or include "stitching markers" as known in the art. Markers 22 may be fixed or removable as described further herein. In some embodiments, shield 18 may have a base platform or step for supporting a patient, as know in the art.

Shield structure may include handle 28 to allow the operator to easily slide the shield structure (e.g., and shield) in direction SMOV to shield height 40 (e.g., vertically moveable) to provide one or more types of markers at positions on the shield. These markers may include x-ray transparent markings (do not show in captured images, such as lines 24) for identifying detector positions, such as at borders of image areas 42A-C, between source 12 and detector 16; and for identifying center of image overlap areas to identify placement of processing software identifiable makers (e.g., x-ray image able markers, such as markers 22) or markings may be placed on outer edges of shield or shield frame or and markings for tube laser alignment to the center of image areas. Marker 22 positions in images of image areas 42A-C can be used for connecting (e.g., overlapping or stitching) the images, such as based on the marker positions within the overlap are of each adjoining image. In some cases, height 40 represents the height from the floor (or a platform the patient stands on) to the top of the shield. In some cases, height 40 represents the height from the floor (or a platform the patient stands on) to the top of the shield 18. Handle 28 may represent one handle on a side surface of column 35 as shown, or on shield 18. Handle 28 may represent one handle, two handles (one on each side), or a grip area for the user to easily grip the column or shield (e.g., one or both sides with a hand) without interfering with the patient, detector or stand positions. In some case, the column or shield includes a handle or gripping location to be manually gripped by a user to vertically move the shield along the rail, to locate the shield at a desired shield height that positions the markers at vertical borders of the image areas.

In some embodiments stand 20 includes a motorized system, an electromechanical system, or a pulley system to allow the user to easily move the shield structure to selected height 40, such as by pushing "up" and "down" buttons on stand 20. In some embodiments the button are on the back or side of rail 26. In these cases, handle 28 may stick out through an opening in the back or side of rail 26. In some embodiments, the shield structure may be "automatically" vertically moved or positioned along direction SMOV by such a system. In some cases, the movement may be controlled by the user at control unit 23, and moved by motors and/or other components of stand 20. This may be based on the height of markers 22. In some embodiments, during exam, first the shield height is set to preferred range of anatomy coverage area (once set to this "patient height", the shield height stays at this height for the entire sequence of images) then the chest detector holder/bucky is manually aligned to corresponding markings on the stand (e.g., markings 25A, B or C) or to simplified mechanical detents for each image to be captured. In some cases, both markings and detents may be used to provide a double check or confirmation of the position. In some embodiments fewer than 3 markings are used to align the detector, such as where only a top and bottom marking are used; where only one marking is used; or where no markings are used and the detector is aligned based on the size of the glass, when using detector position detents. Shield height may be adjusted by manual sliding movements within the outer shield rails. Rail friction and/or counteraction by way of flat coil spring or other known mechanisms may be included to simplify movements and counterbalance weight of typical detector and optional grid. Some embodiments may include motorized or free-fall movement for the shield.

Shield structure 34 (e.g., column 35) is movingly coupled to rail 26, such as by mounted between two parallel rail surfaces of rail 26 which are mounted on stand base 32 or being movably mounted on one column. Mounting of rail 26 to base 32 may maintain a parallel disposition of rail 26 so that shield structure 34 can be moved by the user along vertical height SMOV (e.g., slidably moved along a vertical axis) to position the top of shield 18 (e.g., the top or uppermost part of surface 19) at shield height 40 of possible shield heights 41 (see FIGS. 2A-B). In some cases, heights 41 represent a range of heights of the top of the shield. Heights 41 may be selected to provide enough range for a selected desired image area and height of patients, such as up to 6 foot 6 inches tall, or taller in some cases. Shield 18 may be described as an imaging or patient support "member" or "screen".

Total image area 44 may correspond to or cover a desired total image area of a patient to be imaged during an imaging exam. Area 44 may be selected by vertically moving shield structure 34 in directions SMOV on or along vertical rail 26 to shield height 40 using handle 28 so that at height 40, the shield provides at least two or three vertically adjacent image areas (e.g., of areas 42A-C) that are centered on and include the desired total image area. Vertically positioning shield structure 34 so that shield height 40 provides these image areas may be dependent upon or based upon the total height of patient M. In some cases, the shield structure 34 may be moved to (or positioned at) a shield height 40 that is selected based on a height of anatomy of a patient that is desired to be imaged (e.g., in the desired total image area). It can be appreciated that for the same anatomy desired to be imaged, the height of that anatomy may be different for different patients. This may be due to different patients having different height, and/or having the same anatomy at different heights, and to accommodate for long length images of upper or lower body areas (e.g., even for same height patients). In certain cases, the shield structure 34 may be positioned at a shield height 40 such that a vertical range of anatomy of a patient that is desired to be imaged is within a desired total vertical image area of the shield. In some cases, selecting shield height 40 may include vertically aligning markers 22, of one or more adjoining image areas, to be above and below a height of anatomy of a patient that is selected to be imaged in a desired long length image. In some cases, frame 30 and shield 18 will be have a total vertical size (or height) so that possible shield heights 41 and the vertical size of shield 18 are sufficient to image a desired extended field of view or vertical height of a person's anatomy for a long length imaging exam, such as known in the art. In some cases, heights 41 extend from a height of the shield that images starting as low as from the floor up 2-3 images or more or starting from top height of to up to a height of for example 6 foot 6 inches in height (depending on height of stand which can be design in different heights) and imaging 2-3 images or more in length down. Area 44 may be a portion or a subset of the maximum image height field provided by heights 41. Sequence or travel direction up or down from one image to the next may be irrelevant to the stand design (image processing software may have a preference for easier combining of the images). In some cases, the shield may have a range of capture area. This range may be equal to the total area of surface 19. This range may define the total desired image area, as within the shield's range of capture area.

The patient's height or the height of anatomy of a patient that is desired to be imaged may be determined by a prior height measurement or by the height observed by the user while the patient is actually standing at location 14. In some cases, the height of anatomy of a patient may be determined by the user, as known in the art. In some cases, the height of anatomy of a patient may be determined based on internal and/or external anatomy of the patient. After the imaging exam, the shield structure 34 may be moved to a different shield height for a subsequent exam of a different height patient.

Wheels 33 allow stand 20 to roll along or be moved across a floor. In some embodiments, wheels 33 may be castors having rotational locks, as know in the art. Thus, stand 20 may be a "portable", "mobile" or "moveable" stand that can be moved between different exam rooms and/or can be used with different source systems. Wheels 33 may be optional, and base 32 may be slide-ably mounted (or otherwise movable) on the floor. Location 14 may be between two arms of base 32. Additionally, a patient step platform may optionally be used between the legs of the stand base (32) to raise the viewability of the patient's feet to a desired height above the floor.

According to embodiments, stand 20 is horizontally positioned (e.g., rolled or positioned horizontally) in front of source 12 so that shield 18 (or image areas of the shield) is horizontally centered with the horizontal center or axis of an image taken when irradiating the detector with the source. Then Patient M may be horizontally located (e.g., moved or positioned horizontally) at patient standing location 14, between shield 18 and source 12 so that the areas of the patient to be imaged are horizontally centered with the horizontal center or axis of the image areas of the shield. This may include arranging the patient in a standing position. Positioning the patient may also consider horizontally positioning the patient between detector holder 37 (or detector 16) and source 12 so that areas of the patient to be imaged are horizontally centered with the horizontal center or axis of an image taken when irradiating the detector with the source. In some cases, the patient is horizontally aligned between the source and the shield (and detector) so that a desired total image area is centered within horizontal center of the actual total image area 44. In some embodiments, the desired total image area may be a planned long length image area, such as known in the art. It may also be based on a user's determination (e.g., an x-ray technologist or radiologist) of examining the patient while the patient is at location 14.

According to embodiments, shield column 35 includes vertical detector rail 50 for holding detector holder 37 that is able to hold detector 16 to receive radiation emitted by a radiation imaging source in front of the stand and patient. Rail 50 may be part of or fixed onto column 35. Detector holder 37 may be described as a "frame" for holding the detector. Holder 37 may include a detector holder mount (not shown) movably coupled to rail 50 so that holder 37 can be manually moved vertically along rail 50, behind shield 18. Thus, arms 31 may locate shield 18 far enough forward, in front of rail 50, so that holder 37 is free to move in vertical directions IMOV, along rail 50 to positions to image desired image areas, such as areas 42A-C. Holder 37 may hold detector 16 at a relatively fixed location and height with respect to holder 37.

Such a holder may include structures for mounting of direct x-ray capture flat panel detectors or CR computed radiography or analog screen film cassette, such as detectors that can be removed from holder 37 and used in another stand or holder. In other embodiments, the holder 37 can feature a fixed built-in (not removable) detector. In some embodiments, the detector and the mounting of the detector on holder 37 may include structures known in the art for flat panel detectors. The detector holder may also include the ability to fit an anti-scatter grid attached to or in front of the detector as commonly used for these types of exams.

In some embodiments holder 37 is moveably coupled to rail 50 to be manually moved vertically to position the detector holder at a vertical position or height based on the vertical position of the markers (e.g., as shown by marker lines and/or marker pointers). Thus, holder 37 (and a detector in the holder) may be manually moved in vertical directions IMOV to position detector 16 at a detector to provide images of desired image areas, such as based on marker positions, so that the images have enough overlap to be combined. Detector holder 37 may be constructed in such a manner that it can move along rail 50 provided in parallel to the body axis of the patient. In some cases, the detector holder 37 is described as "integrated" with, and part of the positioning stand 20 structure. Detector may be vertically slidable in directions IMOV along a vertical axis. In some cases, the vertical axis that the shield is moveable on (in directions SMOV) may be parallel to the vertical axis for the detector (in directions IMOV).

Holder 37 may be movingly coupled to rail 50, such as by being movably mounted on one, or mounted between two parallel rail surfaces of rail 50 which are mounted on column 35. Mounting of holder 37 to rail 50 may maintain a parallel disposition to rail 26 so that holder 37 can be moved by the user along vertical height IMOV (e.g., slidably moved along a vertical axis) to position the top, bottom or midpoint of holder 37 at a holder height of possible holder heights. These heights may correspond to the image areas of the shield.

In some embodiments, the user manually adjusts the height of detector holder 37 by moving it along vertical direction IMOV, over a range of detector heights for patient M during the x-ray exam. Detector holder 37 may include detector holder handle 36 for such manual movement.

Handle 36 may allow the operator to easily slide the holder (e.g., and detector) in direction IMOV. In some cases, the range of heights that holder 37 can move over represents the height of a long length image or of a total image area 44. Handle 36 may represent one handle on a side surface of holder 37 as shown. In some cases, handle 36 may represent two handles (one on each side), or a grip area for the user to easily grip the holder (e.g., one or both sides with a hand) without interfering with the patient, shield or stand positions.

The height of the detector holder may be moved to locate the detector holder at a detector height position determined by or based on the positions of markers 22 on the shield (e.g., once the shield is positioned at height 40 as noted herein). In some cases the detector holder is positioned to image an image area as described herein. Once the shield is at height 40, the detector holder may be moved to different detector holder height position to image different, subsequent image areas (e.g., of areas 42A-C) while the shield stays at the same height 40, for a patient. In some cases, markers 22 may be used to identify a vertical height for alignment of the detector holder (e.g., to one or more borders of an image area; or to a center of an image area), such as by aligning a vertical edge of the detector holder with a height of markers 22 for an image area. In some cases, the stand (e.g., rail 50) may include mechanical detents 53 (e.g., openings or holes in the sides of the rail) to simplify precise positions. For example, detents 53 may be located at heights along rail 50 to be engaged by one or more pins 54 of holder 37 so that the holder can be repeatedly located and removably locked in at (e.g., 3) predetermined heights for proper imaging. This may be done to align the detector holder for proper overlap amount for each exposure, and/or for alignment of images. This may include aligning the detector holder to provide a proper overlap amount of each image so that the adjacent images can be aligned and combined. In some cases, alignment of the detector holder may be based on or may include being based on the height of anatomy of the patient that is desired to be imaged. Such use of detents and pins may provide quicker, easier and more efficient movement of the holder between the detent/stop positions, than other means. This may dramatically simplify fast, easy consistently accurate alignment of the detector from one position to the next. This may take the guesswork out of trying to visually align to markings on the outer edges or on the glass. It may also eliminate mistakes from not overlapping correctly and simplifying correct position of the marker locations in the images. In other cases, other stops or means of indexing could be used to replace the detents, but provide the same functionality.

For instance, the detector holder may be vertically aligned or positioned so that the top, bottom or middle of the detector is vertically aligned with one of markers 22 (e.g., such as by being vertically aligned with one of lines 24 and/or pointers 25 based on a user's observation). In some cases the detector holder may be vertically positioned to, or be vertically aligned with (e.g., relative to) more than one of lines 24 and/or pointers 25. This may include selecting two of lines 24 and/or pointers 25 from the top, bottom or middle of the image area are vertically aligned with two positions (e.g., at top, bottom or middle) of the detector holder. There may be markers or markings on the front and/or sides (e.g., at top, bottom or middle) of the detector holder to align with the markers or markings on the shield.

In some cases, the detector holder may be vertically aligned or positioned using holes or other common forms of mechanical detents at fixed vertical locations that are engaged by pins of holder or other forms of detents. In some embodiments, the detent and pin structures may be those known in the art for such purposes. These locations may be at predetermined heights based on the vertical and horizontal size of known detectors. The known detectors may be or include a selected number and type of detectors desired to be used with stand 20. In some cases, this may include rail 50 having vertical fixed precise detent positions to allow movement of holder 37 to (and locking into position at) the exact measured positions of a detector holder, as required for accurate overlap of the images based on the type of detector device, its size and its field of active capture area. Use of these detent positions may be confirmed by or based on a user's vertical alignment of the holder or detector with one of lines 24 and/or pointers 25, such as based on a user's observation.

In some embodiments rail 50 and holder 37 include a motorized system, an electromechanical system, or a pulley system to allow the user to easily select height 40, such as by pushing "up" and "down" buttons on stand 20. In some embodiments, the detector holder may be "automatically" vertically moved or positioned along direction IMOV by such a system. The movement may be controlled by control unit 23, and moved by motors and/or other components of stand 20. This may be based on the height of markers 22 or side markers 25. In some cases, the detector holder is similar to the detector bucky of a typical chest stand imaging device. Movement distance of the chest bucky from one image to another may be determined by the detector model. In some cases, movement of the holder is accomplishable by manual movements. In some cases the cart features motorized elevation movements of the detector, which can be by button controls mounted to the cart, or by wireless or wired remote hand or foot switches, which may move the detector to electromechanically controlled detents or stop points, or aligned by user visually aligning movements to alignment markings on the detector holder and shield assemblies.

Descriptions above for vertically positioning or aligning the detector holder at a height may also be used to describe aligning the detector holder to position the detector at the height described (e.g., the same position as described for aligning the holder). This may include moving the detector holder in direction IMOV to position or align the detector at a detector height position, using the process and/or at the height describe for the detector holder.

Support rail 26, column 35 and rail 50 may be rigid metal tracks. Rail 26 may be part of the stand structure connected to the base of the stand. Patient shield is held within these outer side rails and travels up and down them, such as with a resistive friction that is based on felt type of material lined inside of rails to provide sufficient friction to hold the shield from slipping once a desired height is set. In some embodiments, patient shield 18 is attached to shield structure 34, structure moves up and down frame column rail 26. Detector holder 37 moves up and down detector rail 50. According to embodiments, one or both assemblies (shield structure and detector holder) may utilize commonly known motorized travel (such as worm gear drive or other commonly known) or manual friction mechanical systems (such as cable(s) or metal bands and counterweights or other friction based mechanisms) for such movement. For some cases, motorized travel is used for shield and or detector travel structure, with electric motor and worm gear drive engaging the structure and rail 26, controlled by wired remote having up and down buttons; and the detector holder travel may be based on (e.g., uses) a spring loaded metal band counterbalanced by its spring or coil band inside of detector rail 50, the band engaging the holder and rail 50. In this case, the holder may move up and down to be located and removably locked into position by the detent and pin structures, such as noted herein.

In some embodiments, detector 16 may be a radiographic image "imager" or "sensor" as known in the art. In some cases detector may be a flat panel radiographic detector, or a radiographic image sensor to produce image of an image area or field equal to or just smaller than the total surface area of the detector. In some cases, detector 16 may be a detector for traditional CR, a re-useable computed radiography (CR) imaging plate, or an analog x-ray film screen cassette, as known in the art. In some cases the detector may be a customer's existing digital capture device such as a flat panel detector (fixed or removable) or CR cassette combined with the associated computerized image processing workstation (e.g., control unit 23), as known in the art.

Detector 16 may be an image radiation detector or image sensor (e.g., similar to that of a typical chest stand imaging device) able to produce images of the image areas (fields or frames). The images may be connected by stitching together or combining the adjoining images, such as by overlaying vertical borders of the images with or without software or user recognizable markers so that the markers shared by overlapping borders of vertically adjacent areas are overlayed in the images to correctly match alignment from one image to the next. For instance each of a plurality of the radiographic images (of image areas) may partially overlap another image at the overlapping parts within total image field 44. Stand 20 provides radiographic image areas for the total image field 44 of a patient, the total image field being longer than a length of each image (a maximum field of view of an imager, radiation detector or sensor to produce image of an image area or field). In some cases, each image area may be equal to the maximum field of view, image area, or surface area of the detector.

In most cases, control unit 23 is not connected to the stand. Typically the control unit is connected to the source generator, it sets exposure techniques and triggers exposure. In some cases, the detector user workstation is connected to the control unit 23 to simultaneously control other automation such as x-ray source and detector repositioning movements from one capture to the next, such as known in the art. Workstation may also through communication to the Control unit 23, control presetting preferred exposure technique settings, start, exposure duration, beam filtering, and other processing of radiation detection by detector 16. In the example of DR digital capture detectors, the image signals output by the detector are converted to digital data and transmitted to the workstation via wired or wireless connection where images are previewed and subjected to image processing, including combining of images of image areas and sent to other workstations for diagnosis and archiving.

FIGS. 2A-B show front and side views of example embodiments of a portable patient positioning stand for multiple image areas of a total radiographic image area or field. FIGS. 2A-B show stand 20 including frame 30 having rail 26, base 32, wheels 33 and identifying location 14. They also show column 35 having handle 28 and vertically moveably attached to rail 26; and arms 31 attached between the column and shield 18. The shield has surfaces upon which markers 22A-C, marker lines 24A-C, and marker pointers 25A-C are located. For instance, in some cases markers 22 and marker lines 25 are located on front surface 19 of shield 18. In some cases marker pointers 25 are located on the back or side surface of shield 18. FIGS. 2A-B also show rail 50 attached to column 35, and holder 37 having handle 36 and vertically moveably attached to rail 50. Detector 16 is shown mounted in or held by holder 37. Shield 18 and holder 37 may be moved over (e.g., to cover) the vertical total range of shield heights 41, such as to locate or image total image area 44 within (e.g., to cover) heights 41. In some cases stand 20 of FIGS. 2A-B may be or have the same components described for stand 20 of FIG. 1.

FIGS. 2A-B show shield structure 34 (e.g., column 35) movably mounted on surfaces of rail 26. Shield structure 34 may be moved to cover any of heights 41 along vertical height direction SMOV, such a by being movably arranged along surfaces of rail 26 to be positioned at height 40. In some cases, height 40 is selected based on a height of anatomy of the patient that is desired to be imaged, the position/area of the desired images, and the number of images, so that the markers provide software recognizable marks in images including the image areas for connecting the images. The markers may provide the marks, such as by marking or identifying vertical borders of image areas; and/or allowing the user to image enough overlap of a border in two adjacent images for computer software to automatically recognize the markers and/or overlap to accurately combine the images to form a single image including the two areas.

In some embodiments, rail 26 has one or more rigid metal tracks connected to the base of the stand. Parts of the shield structure may be held within these tracks and travel up and down them, such as by motorized means; and have a resistive friction, detents and/or indexing means engaging the tracks to provide sufficient holding force of the shield structure to keep it from slipping once a desired height is set. In some cases, column 35 is vertically moveably mounted or attached to rail 26 by movable mounts such as wheels, bearings, or flanges that extend into and move along recesses in the inner or front surface of the rail. These mounts may roll or slide within or along the rails while they maintain mounting of the shield on the rails. In some cases, the mounts may form a shape around sides of the rails, such as a "C" or "[" shape that maintains mounting of the shield on the rails. The vertical position or height 40 of the shield structure 34 may be maintained on rail 26 such as by the mount including an anchor, pulley, or friction. For instance, a clamp or spring loaded pin or other mechanism may be manipulated by the user to lock column 35 at height 40. In some cases, a pulley system, counter weight system, shock absorber system, spring system, or hydraulic system (e.g., within rail 26) may counter the weight of the shield structure (and detector) so that it does not move once stopped at position 40 by the user. In some cases, an amount of friction between the mount on the column and the rail will maintain the position of the shield structure once it is stopped at a position by the user. Maintaining the position of the shield structure may include maintaining it with enough force to support the patient as described herein. In some embodiments, these mounts may be or include those known in the art for such moveable mounting purposes.

Shield 18 may support the patient, and optionally cooperate with handles or armrests (not shown) for supporting arms of the patient. In some embodiments, armrests may be coupled to shield 18, and may be foldable handles for resting the patients arm on, such as know in the art. In some cases, the armrests may be attached to shield 28 and move with the shield. The armrests may be height adjustable (e.g., slidingly mounted) on the sides of the shield for independent height positioning (e.g., similar to how the shield structure is movably mounted). In other cases, the arrests may be positioned to be just below the height of shoulders or elbows of the patient to support the patient's arms or forearms.

In some cases, detector holder 37 is vertically moveably mounted or attached to rail 50, such as described above for the mounting of column 35 on rail 26. The vertical position or height of holder 37 may be maintained on rail 50 such as described for the mounting of column 35 on rail 26. This may mounting structure to ensure that holder (and detector) does not move once stopped at the holder position 40 by the user. In some embodiments, these mounts may be or include those known in the art for such moveable mounting purposes.

In some cases, holder 37 has holder rails 52 to hold the detector. In some cases, rails 52 are moveable to adjust in position to hold various sized detectors and to hold detectors at different orientations. Moveable holder rails may be vertically aligned or positioned using holes or detents at fixed vertical locations along holder 37 that are engaged by pins of rails 52. In some embodiments, the detent and pin structures may be similar to those described for detents of rail 50 and pins of holder 37. In some cases, they may by those known in the art for such purposes. These locations may be at predetermined heights based on the vertical and horizontal size of known detectors, so that the images of the image areas include enough overlap to accurately combine the images to form a single image, such as described herein. Such an overlap may be about 1-2 inches; or at a specific amount determined by software preferred tolerances for example between 1 and 4 inches. The known detectors may be or include a selected number and type of detectors desired to be used with stand 20. In some cases, anti scatter grid covers may also be used attached to or in front of the detector as commonly preferred for these exams. In some cases, this may include holder 37 having vertically fixed precise detent positions to allow movement of rails 52 to (and locking into position at) the exact measured positions of a detector, as required for accurate overlap of the images based on the type of detector device, its size and its field of active capture area. Use of these detent positions may be confirmed by or based on a user's vertical alignment of the detector with one or more of lines 24 and/or pointers 25, such as based on a user's observation.

Shield 18 may include fixed or typically preferred stick on or moveable markers 22 such as special shapes of marker material to identify (e.g., provide, demarcate, or mark) borders within overlap area of or between vertically adjacent radiographic image areas. Markers 22 may be arranged at horizontally wide enough (e.g., spread out) positions with respect to the patient's width so that the markers do not overlap with the image of the patient (e.g., anatomy) taken by the detector and/or so that they are not cut out of the imageble field when x-ray source field is collimated close to outer edges of desired region of interest patient anatomy. In some embodiments, markers 22, may have a cross shape, or any specific recognizable shape preferred by image processing software, such as those known in the art. For some embodiments, an "X" or "+" plus sign marker may be positioned on the right and left side of the outer edge of the area of the shield (e.g., at a horizontal outer border of the shield) where the multiple images will be captured at an overlap to each other. Each marker 22 may have a size determined by software preferred tolerances for example of at least 10 mm or larger or similar. In some embodiments, the markers may be described as "stitching markers" to align or stitch together the adjacent multiple images, image borders, image edges, or image boundaries, as known in the art.

Shield 18 may also include marker lines 24 such as lines of radiation transparent material (low attenuation coefficient, not visible in the resulting image) to be used as Detector Alignment Markers, such as by identifying borders of radiographic image areas (e.g., in addition or independently of markers 22). Shield 18 may also include marker pointers 25 outside or within of the field of detectable view. If within field of view, such as shapes of radiation transparent material (low attenuation coefficient, not visible in the resulting image). These markings may be used as Side of Stand Alignment Markers, such as by being at the same height as markers 22, but on side or back surfaces of shield 18 to identify borders of radiographic image areas (e.g., in addition to and corresponding with the height of markers 22). The marker pointers may be attached to the front surface, side or back of the shield; or disposed through the shield to be visible to the user from the side and back of shield. In some cases, the pointers are shaped like a nail, arrow, or pointer protruding from the stand and pointing backwards towards the detector. Pointers 25 may allow the user to more easily identify the height of the markers (and marker lines) from a position beside or behind the shield. This allows the user to more conveniently and efficiently move and locate detector holder 37 and detector 16 for the image areas. In some case, pointers 25 may be markers or markings that extend to or include markers on the back of the shield to assist user in locating the detector holder and detector to the correct height position based on shield markings 22, such as by having pointers 25 at the same height as shield markers 22 on the front of the shield. Markers 25 may have a shape and size similar to that described for markers 22.

Stitching Markers 22 (A, B, C) typically are formed of (Pb) lead (which has large x-ray attenuation coefficient) so that they are recognizable in the image by the software which utilizes them to align the images and stitch or seam the adjoining images together. Markers 22 may be or include other substance with a large radiation attenuation coefficient. Being recognizable by the software be included in or a result of the markers identifying a border of an image area. Detector Alignment Markers or marker lines, 24 (A, B, C) are formed with x-ray transparent material (low x-ray attenuation coefficient, not visible in the resulting image) such as simple screen printed lines on the shield. Side of Stand Alignment Markers, or marker pointers 25 (A, B, C) may include a metal or plastic or similar material and act as visual mechanical guides (e.g., for the user) near or touching the shield alignment to the detector, to additionally simplify aligning the detector to the shield, (these are not in the image area and do not require any special material).

Markers 22 are shown in FIG. 2A as markers 22A identifying a border between image areas 42A and 42B; and markers 22B identifying a border between image areas 42B and 42C. In some cases, these borders may be used to mark images so that adjacent images can be combined (e.g., automatically or manually, using software) and/or to allow the user to position the detector to ensure enough image area exists over a border so that adjacent images can be combined (e.g., automatically or manually, using software). Marker lines 24 (e.g., Detector Alignment Markers) are shown in FIG. 2A as marker line 24A identifying a border between image areas 42A and 42B; and marker line 24B identifying a border between image areas 42B and 42C. In some cases, these borders may be used to position the detector holder and detector to correct image areas (e.g., as noted above for markers 22A-B) so that adjacent images can be combined. Marker pointers 25 (Side of Stand Alignment Markers) are shown in FIG. 2B as marker pointer 25A identifying a border between image areas 42A and 42B; and marker pointer 25B identifying a border between image areas 42B and 42C. In some cases, these borders may be used to position the detector holder and detector to correct image areas (e.g., as noted above for markers 22A-B) so that adjacent images can be combined. In some cases, the width between markers of markers 22A and B is selected based on the width of patient M and or the width of a desired total image area.

Although positions 38A-C and areas 42A-C are shown as three corresponding positions/areas, they may represent two or more corresponding adjacent positions/areas. In some cases they may represent only two corresponding adjacent positions/areas, such as 38A/B and 42A/B. In some cases, markers 22 may optionally include markers at the top border of area 42A and/or at the bottom border of area 42C (e.g., such as shown in FIG. 1). As shown in FIGS. 2A-B, some embodiments include markers 22C, marker lines 24C and marker pointers 25C, such as for identifying a border between area 42A and an area above area 42A. In some cases, markers 22C, lines 24C and/or pointers 25C may define a border between image area 42A and a similarly sized additional image area above area 42A. This additional image area may be used to image more height of a tall person or from floor to waist such as in long leg exams, or the typical image is for scoliosis exams covering the neck and spine. In these cases, the height of the patient's long leg exam area, or the height of the neck and spine for typical images for scoliosis may be considered the height of anatomy desired to be imaged. In some embodiments, markers 22 may be positioned on shield 18 as known in the art.

In some cases, descriptions herein of the use of "markers" or "markers 22" include the use of markers 22 and pointers 25. In some cases, descriptions herein of the use of "markers" or "markers 22" include the use of markers 22, lines 23, and pointers 25. In some cases, descriptions herein of "markers 22" include alignment lines at the same vertical height described for markers 22. In some cases, descriptions herein of "markers 22" include mid-level markers between adjacent vertically positioned markers 22 and at the left edge and right edge of shield 18 (e.g., not shown). The mid-level markers may be used to identify a vertical height for alignment of the x-ray tube to the center of each image area, such as by aligning the vertical center of the tube's output radiation and/or by using it's laser centering line (if it includes one) with the mid-level marker for an image area. These mid level markers may include marker pointers that function similar to pointers 25, and help with detector holder and/or source vertical alignment. Other appropriate positions of markers are also considered.

According to embodiments, based on the relative locations of markers 22 on the shield, the height range of anatomy of a patient that is desired to be imaged and desired area 44, the shield 18 can be moved to height 40 so that the marker positions in images of image areas 42A-C can be used for combining the images (e.g., areas 42A-C) of total image field 44 of patient M by overlapping the vertical location of a pair of markers 22A, B, or C as shown in adjacent figures. Moving to height 40 may also be based on ensuring that there is enough overlap of images of image areas of field 44 for connecting the images. The markers may be located with respect to each other on the shield so that the markers divide the total shield height into multiple vertical image areas, such as by demarcating, marking, or define a border of or between two image areas. Each image area may be described as an image "capture", "field", "view", or "frame". In some cases, the markers are easily located by the user or a computer in each of the images of an image area.

Control unit 23 or manual movement switches may be used to align multiple images or image areas of a total image or total image area, such as described herein. In some cases, control unit 23 may be connected to a digital x-ray workstation that features the ability to display, reprocess and send images to diagnostic workstations. In some embodiments, the alignment between vertically adjacent images (e.g., of image areas 42A-C) is recognized by software of a digital x-ray workstation, by utilization of the special shapes of makers 22 or without markers identifying a specified typical overlap area and or recognition of anatomic structure. Once the separate images are captured, the software looks for the markers and lines them up with the sequential images captured to accurately reproduce the overlap and align them together. In some cases, a different workstation or computer may be used to aligning the multiple images.

Descriptions above for vertically positioning or aligning the detector holder at a height may also be used to describe aligning the detector holder to position the detector at the height described (e.g., the same position as described for aligning the holder). This may include moving the detector holder in direction IMOV to position or align the detector at a detector height position, using the process and/or at the height describe for the detector holder.

In some cases the imager (e.g., detector 16) may be a typical size such as 14 inch tall by 17 inch wide or square such as 17×17" flat panel detector. In typical uses the detector may be oriented for 14 inch wide by 17 in tall images. In some embodiments, the stand may be designed with its lines configured for 14×17 or 17×14 detector use. Height and width of stand and/or shield are not dependent on detector size. Height can be based on typical patient height ranges needed. Width can be based on typical widths of chest buckys and/or detectors common which currently utilize larger size detectors for these types of exams (DR, CR or film screen) such as 17×17 or 14×17 or similar. Detector stands that feature removable detector, typically will hold any size detector. As an example a 14×17 or 17×17 embodiment may feature a stand 78 inches high, and 29 inches wide; the shield may be 48 or 51 inches high and 14, 17 or 26 inches wide; the image areas defined by the markers may be 17 inches high with the center of marker overlap areas positioned at 15.5 inches and the adjustable width between markers may be 12 inches typical or less based on patient width. In some cases, the space above markers 22C to the top of the shield may be 1 or more inches or even flush with the line; and the space from a marker to an image centerline marker may be center of a 14 or 17 inch depending on orientation. Some embodiments of stand 20 may apply to a 17 inch tall by 17 inch wide flat panel detector to provide wider anatomy coverage. In some embodiments the stand may fit either 14×17 portrait orientation or 17×17 without changes to the markings or stand dimensions. Stands may be designed for any size detector.

FIGS. 3A-B are side views illustrating example embodiments of a system for taking a long length of image of a spine using a portable patient positioning stand for defining multiple image areas of a total radiographic image area or field. In some cases the process of FIGS. 3A-B may include using system 10 as shown in FIGS. 1-2. FIG. 4 shows example embodiments of a process 400 for taking a long length of image of a spine using a portable patient positioning stand for defining multiple image areas of a total radiographic image area or field. In some cases the process of FIG. 4 may include using the system as shown in of FIGS. 3A-B. Process 400 may include using a portable positioning stand to position a patient and to locate a radiographic detector at multiple positions to create multiple images of multiple image areas identified by markers of a shield of the stand.

At block 405 a portable stand (having a shield with markers and a detector holder) is located to be radiated by a source of radiation. Block 405 may include locating a portable positioning stand so that a vertically adjustable shield of the stand having markers, and a vertically adjustable detector holder of the stand can be positioned to locate a radiographic detector at multiple positions to create multiple images of multiple image areas identified by the markers. Block 405 may include horizontally aligning the stand in front of source 12 as noted herein. In some cases, block 405 includes, as illustrated in FIG. 3A, positioning shield 20 and detector holder 47 so that the detector will properly image the patient M standing with his/her back against the shield as noted herein.

Then, (e.g., next in time during process 400) at block 410 a patient is located in front of the mobile patient support stand. Block 410 may include locating or positioning patient M at standing location 14 as described herein. In some cases, block 410 includes, as illustrated in FIG. 3A, positioning the patient M to stand with his/her back against (e.g., touching and possibly supported by) the shield 18 (and optionally armrests). In some cases, the patent may be located on a stand or block place on the floor between arms of the base of the device, in order to image lower parts of the patient, such as the including the entire patient's foot in the image.

Then, at block 420 the shield structure of a portable stand is vertically aligned (e.g. manually moved or positioned) to position a shield of the structure at a correct shield height based on the height range of anatomy of a patient that is desired to be imaged and the vertical height positions or locations of markers on the shield (e.g., such as markers 22, 24, or 25). In some cases, block 420 may include manually vertically locating the shield (e.g., by moving the structure) to a desired height based on the desired total image area, and/or a desired height range of anatomy of a patient that is desired to be imaged (e.g., imaged within the total image area). This may include selecting height 40 so that anatomy of a patient desired to be imaged is vertically located within the vertical range of two or more image areas (e.g., within areas 42A-B, or 42A-C if 3 areas are needed). Block 420 may include vertically locating the shield at height 40 (possibly using handle 28) as described herein. In some cases, block 420 includes, as illustrated in FIG. 3A, manually moving the shield to a desired shield height to arrange markers 22 at borders of desired image areas of a total image area, based on a height range of anatomy of a patient that is desired to be imaged and a determined total image area 44. In some cases, Block 420 may include positioning or moving removable markers on shield 18 as described herein.

Then, in some embodiments, source 12 may be moved up and/or down along a vertical axis (e.g., using motors and control unit 23) to be located at the desired source height so that it is vertically aligned at the same height as the center of total image area 44. For example, the shield may have been set in a height position, by the user (not illustrated) to enable detection of an X-ray at area 42A that has passed through the chest of the subject M. Here, the patient's chest may be in (e.g., define or describe) a height range of anatomy of a patient that is desired to be imaged. This optional process may be part of block 420 or part of block 440. In other cases, the source is only rotated to provide proper output vertical radiation to irradiate the detector (e.g., see block 440). In some embodiments, block 42 includes vertically centering the radiation source height to a height of a vertical center of the total desired image area within the shield's range of capture area.

Then, at block 430 the detector holder of the stand is vertically aligned (e.g., manually moved or positioned) to align a detector held by the holder to a first detector height position based the vertical position of the markers and or mechanical detent position. This may include moving the detector holder to align the detector to a first image position or area based on first marker positions. Block 430 may include manually vertically aligned the detector (e.g., by moving the detector holder) to an image position or area (e.g., area 42A) as described herein. In some cases, at block 430, the detector holder is manually vertically aligned or moved to locate the detector at a correct detector height to capture an image of a first image area (e.g., area 42A) based on marker positions 22. Block 430 may include aligning the detector to an image position (e.g., position 38A) so that the detector images an area including at least the first image area (e.g., area 42A). It may also include aligning the detector based on the vertical location of markers, lines, or pointers so that the detector images an area including at least the first image area (e.g., area 42A). In certain cases, block 430 may include aligning detector 16 based only on lines 24A, or pointers 25A. In some cases, detector 16 may be aligned based only on the position of marker pointers 25. FIG. 3A, illustrates and example where detector 16 is manually set in a position by the user, enabling detection of an X-ray that has passed through the chest of the subject M, based on markers 24A and/or 25A. Aligning to the first position may include alignment of detector to 22C or 24A as a top of the image field reference, or aligning from the bottom up aligning the bottom of image area with the as a bottom of image area 42C or to marking 24B as the starting reference.

The movement of the shield structure in block 420 may be independent with respect to the detector holder height or movement of the detector holder. Also, the movement of the detector holder in block 430 may be independent with respect to movement of the shield structure, but may depend on the height of the shield structure and shield.

Then, at block 440 the patient is irradiated to create a first image at the first image position or area. Block 440 may include aligning the radiation output beam of source 12 (such as by rotation ROT) to an image position (e.g., position 38A) so that the beam radiates an area including at least the first image area (e.g., area 42A). It may also include aligning the source based on the vertical location of markers (e.g., markers 22A) and/or the height of the detector or detector holder so that the detector images an area including at least the first image area (e.g., area 42A). Block 440 may include generating or creating an image of an image area (e.g., area 42A) as described herein. In some cases, at block 440, source 12 irradiates the patient, shield 18, detector holder 37, and detector 16; and the detector captures an image of a first image area (e.g., area 42A) including marker positions 22. This image may include markers 22A; or 22A with markers 22B; or markers 22B.

For some cases of block 440, as illustrated in FIG. 3A, an X-ray is applied toward the chest of the subject M from the X-ray source 12 to take an image of the upper half of the spine. In this case the upper half of the spine may be in a height range of anatomy of a patient that is desired to be imaged. For example, source 12 may be aligned to provide image position 38A, such as by vertically aligning height of image position center 39A with that of image center 43A of area 42A.

Block 440 may also include cases where detection signals that have entered detector 16 and are detected by the detector are sent to the detector workstation or detector control unit 23 (not shown). The detector workstation or detector control unit converts the received detection signals to digital signals to generate image data and temporarily stores it in memory (not illustrated). Each of these radiographic images may include images of the markers at its part overlapping the other radiographic image, together with an image of the subject M.

Then, at block 450 the detector holder is vertically aligned (e.g., manually) or moved to align a detector held by the holder to a different (e.g., different than the first) detector height position based the vertical position of the markers or to the next mechanical detent stop. In some cases, this may include moving the detector holder to align the detector to an image position or area based on different marker positions on the shield. Block 450 may include manually vertically aligned the detector (e.g., by moving the detector holder) to an image position or area (e.g., area 42B) as described herein. The different image area may be an image area adjacent to the first area, and that shares a common or same set of markers 22 on shield 18 (e.g., markers 22A). In this case, the detector holder is manually vertically aligned or moved to a different (e.g., different than the first) image position or area based on the same marker positions. In some cases, at block 450, the detector holder is manually vertically aligned or moved to locate the detector at a correct detector height to capture an image of a second image area (e.g., area 42B) based on marker positions 22. Block 430 may include aligning the detector to a different image position (e.g., position 38B) so that the detector images an area including at least the second image area (e.g., area 42B). The different image area may be an image area adjacent to the first area, and that shares a common or same set of markers 22 on shield 18 (e.g., markers 22A). In this case, the detector is manually vertically aligned or moved to a different (e.g., different than the first) image position or area based on the same marker positions. In certain cases, block 450 may include aligning detector 16 based only on lines 24B, or pointers 25B. Other appropriate descriptions above for block 430 may apply to block 450.

For some cases of block 450, as illustrated in FIG. 3B, the shield and source are not moved vertically (e.g., along a vertical axis) since they are already at a desired shield height, such as noted for FIG. 3A. Thus, using the portable stand and/or process 400 (e.g., blocks 405-460) may save time during the process. In some cases, the patient is not re-located. Thus, if the patient does not move by error (during the shortened process), the markers and patent anatomy (e.g., of the desired total image area) should remain the same. This allows the images of the different image areas to be more accurate compared to each other and to be more accurately stitched together. For example, the shield may have been set in FIG. 3A to a height position, by the user to also enable detection of an X-ray at area 42B that has passed through the abdomen of the subject M.

For some cases of block 450, as illustrated in FIG. 3B, detector holder is manually set in a position by the user, enabling detection of an X-ray that has passed through the abdomen of the subject M, based on markers 22A and/or 228. In this case for example, the abdomen may be in a height range of anatomy of a patient that is desired to be imaged.

The movement of the detector holder in block 450 may be independent with respect to movement of the shield structure, but may depend on the height of the shield structure and shield.

Then, at block 460 the patient is irradiated to create a different image at the different image position or area. Block 460 may include aligning the radiation output beam of source 12 (such as by rotation ROT) to a different image position (e.g., position 38B) so that the beam radiates an area including at least the second image area (e.g., area 42B). It may also include aligning the source based on the vertical location of markers (e.g., markers 22A and or 22B) and/or the height of the detector or detector holder so that the detector images an area including at least the second image area (e.g., area 42B). Block 460 may include generating or creating an image of an image area (e.g., area 42B) as described herein. In some cases, at block 460, source 12 irradiates the patient, shield 18, detector holder 37, and detector 16; and the detector captures an image of a different image area (e.g., area 42B) including marker positions 22. This image may include markers 22A and/or different markers 22B. Other appropriate descriptions above for block 440 may apply to block 460.

For some cases of block 460, as illustrated in FIG. 3B, the direction of the X-ray applied from the X-ray source 12 is changed (e.g., rotated in direction ROT) with the positions of the markers (e.g., markers 22B) to apply the X-ray toward the abdomen of the subject M, thereby taking an image of the lower half of the spine. For example, source 12 may be aligned to provide image position 38B, such as by vertically aligning height of image position center with that of image center 43 of area 42B.

Block 460 may also include cases where detection signals that have entered detector 16 and are detected by the detector are sent to the control unit 23. The detector workstation or detector control unit converts the received detection signals to digital signals to generate image data and temporarily stores it in memory (not illustrated). Each of these radiographic images may include images of the markers 22B at its part overlapping the other radiographic image, together with an image of the subject M.

At decision block 470 it is determined whether more images are desired. Block 47 may include determining base on a desired total image area or a planned image area as described herein. In some cases, one or more additional images are desired, such as where the first and additional images of blocks 440 and 460 do not provide image areas of a sufficient or desired total image area. Block 470 may include the user making the determination that more images are or are not desired based on the desired total image area.

If more images are desired, process 400 returns to block 450. In this case, process 400 may continue for another set of different image positions. This other set of different images may include or be to create an image of image area 42C. This continuation may include process describe above for blocks 450-460, but apply to area 42C and markers 22B. It is considered that in some case, a fourth image may be desired to form the desired total image area. Thus, in some cases, the imaging process can be repeated for the number of images required to capture the desired full length of region of interest. Some typical exams may be accommodated with 1 to 3 images. In some embodiments, additional length may be accomplished with a taller stand design with additional detector lengths based on the overall length of the stand.

If more images are not desired, process 400 continues to block 480 and the process ends. Block 480 may include connecting the image areas into a total image area, such as using a detector workstation. For example, one or more image areas may be connected or "stitched" together by vertically aligning markers 22 located on shield 18 between adjacent image areas.

The images may be connected by connecting the image vertical borders, such as by overlaying vertical borders of two adjacent images (e.g., automatically in a computer, or manually by aligning the borders on a display, such as using a computer input or mouse) so that the markers shared by borders (e.g., markers 22A or 22B) of adjacent images of adjacent image areas are overlayed in the images. In some embodiments, such overlaying may include aligning the markers in one image to be displayed over the same markers displayed in the adjacent image, such as is know in the art.

In some cases of block 480 (e.g., in the detector workstation) the image of area 42A (e.g., the upper half of the spine that has been taken first) and the image of area 42B (e.g., the lower half of the spine that has been taken later) are read from the memory, and aligned based on the markers 22A shown within the overlapping parts of the images to connect the two images (e.g., thereby providing one long-length image showing the entire spine). Here the entire spine may define the height range of anatomy of a patient that is desired to be imaged. For cases where image area 42C is also to be connect (e.g., in the detector workstation) the image of image area 42C is read from the memory, and aligned based on the markers 22B shown within the overlapping parts of the images to connect the third image to the other two images. Thus, at block 480, images of image areas 42A and 42B (and optionally 42C) may all be connected (e.g., combined or stitched together) to form an image of total image area 44, such as a desired long length image of a desired total image area.

Although descriptions for process 400 include imaging area 42A, then 42B (then optionally 42C) other orders may be selected. In some cases, 42B will be imaged first, then 42A (then optionally 42C), or 42C (then optionally 42A). Additional areas may be optionally imaged after the ones above. Other orders may include those known in the art.

According to embodiments, x-ray imagable markers 22 may be removable imagable markers that are removably and reusably adhered to shield 18, such as markers having an adhesive backing, adhesive strip, stick adhesive, sticky substance or other structure for temporarily adhering the markers to the surface of shield 18, so that the maker can be easily removed and repositioned on the shield, without inadvertently being knocked or bumped off by the patient or falling due to gravity during an imaging procedure to obtain total image area 44. Removable markers may be manually moveable or positioned so that the markers can be laterally/horizontally moved for different width anatomy or patients. In some cases, these markers are not routinely moved from the shield glass unless the region of interest is significantly narrower or wider than typical exams. They may stay on the glass semi permanently.

In some cases, the removable markers may be positioned at the same vertical position shown in FIGS. 1-3, but are adhered by the user based on a width of the patient, and placement along the outer area of the image and within the area of adjoining image to image overlap, or the combination thereof. In some cases, the removable markers may be positioned at the different vertical position that those shown in FIGS. 1-3, but are adhered by the user based on a height range of the size of the detector or its height orientation, or the combination thereof. This case may apply where the height range of anatomy of a patient that is desired to be imaged is greater or less than areas 42A-C covered by existing heights of markers 22 for a desired total image area.

By being able to manually move or position portable stand 20 having vertically moveable shield structure 34 (and shield) and detector holder 37, embodiments described herein may provide benefits of reduced complication, improved speed of transition from one image location to the next, reduced patient movement, improved accuracy of detector positioning and stitching process, reduced costs and time during imaging procedures (e.g., including obtaining a shield and detector holder in a room for the procedure). They may also lower the cost and complexity of system 10 and components of stand 20. In addition, due to having the shield and detector holder located on a single stand (e.g., with a single base) they may result in fewer inaccuracies in the images and total image area; and more efficient use of the system. They may also provide a more intuitive, efficient and hands on feel and use of the system and stand by the user. They may result in a system and stand that is more versatile, costs less, has fewer components, has less software, has less stitching mistakes and/or better image quality, provides more accurate images, operates more quickly and is easier for the user to use. These benefits are as compared to systems that do not have a portable or manually moveable stand 20 having vertically moveable shield structure 34 (e.g., shield) and detector holder 37; such as systems with shields that are not on the same stand or base as the detector holder, or systems with shields or detector holders that are not portable. For instance, in cases where a very expensive imager is used, portable stand 20 allows that imager to be used more quickly and efficiently, thus allowing more procedures in a shorter time providing more use, profit, and lower labor and other procedure costs. Also, in cases where two or more imagers are used in different rooms, portable stand 20 allows one stand, shield and image holder to be used for multiple rooms, thus lowering procedure costs.

In addition, being able to manually vertically align the shield and detector provide similar benefits as those noted above. This is, as compared to system that automatically (e.g., by computer or controller) moves the shield, and/or detector. Instead, according to embodiments, the height of the shield and detector can be manually aligned instead of being computer controlled. For example, in some cases, (1) the height of the shield can be independently adjusted (e.g., with respect to the detector) for the patient height, (2) while maintaining marker positions (or using moveable marker positions) on a movable shield that are disposed at fixed height positions with respect to each other, to demarcate or identify a plurality image areas; (3) of different imaging positions for the detector, that are selected/planned to be imaged by the user. The process may be further simplified by incorporating of detector position detents 53 (optional) that automate the movement stopping points from one detector position to the next, for faster, easier and more precise repositioning of the detector. Such detents will provide accuracy and repeatability for proper alignment and amount of overlap and location of software recognizable markers from one adjacent location to the next, such as compared to manually trying to align to visual alignment markings.

In some cases these benefits may be realized by a system where only detector holder 37 is manually moved or positioned (e.g., based on height range of anatomy of a patient that is desired to be imaged and/or of markers or marker pointers on the shield), while the shield structure is automatically aligned so that a range of anatomy of a patient that is desired to be imaged is within the desired image area.

The foregoing description of embodiments of the invention has been presented to illustrate the principles of the invention and not to limit the invention to the particular embodiment illustrated. It will, however, be evident that various modifications and changes may be made thereto without departing from the broader spirit and scope of embodiments of the present invention. For instance, portable stand devices, systems, methods of use, and means for performing stand functions and other uses of the stand technologies described herein (e.g., having vertically moveable shield and detector) are considered as possible embodiments of the invention. Moreover, the foregoing stand structures are provided by way of example as they structures used for such a portable stand with an adjustable height shield and an adjustable height detector holder on rails. It will be appreciated that other structures may be used for the stand, such as where two rails are used instead of only one. It may also be appreciated that long length imaging can be used for other than human imaging. The present specification and figures are accordingly to be regarded as illustrative rather than restrictive. It is intended that the scope of the invention be defined by all of the embodiments encompassed within the following claims and their equivalents.

The invention claimed is:

1. A mobile positioning stand for positioning a patient to image a desired total radiographic image area of the patient, the mobile positioning stand providing multiple images areas of the total image area, the stand comprising:
   a stand frame having a vertical stand rail and wheels for moving the stand across a floor;
   a shield structure having a shield column movably coupled to the vertical stand rail to be manually moved vertically along the vertical stand rail, the shield structure having arms to hold a shield having a radio transparent material, the shield having markers, the shield column being movably coupled to vertical stand rail to be manually moved to position the shield at a shield height position, based on a height of anatomy of the patient desired to be imaged, the shield height position selected so that the markers provide marks for aligning an image detector to correct positions for imaging vertically adjacent and partially overlapping images of vertically adjacent image areas of a desired total image area of the patient; and
   a flat panel image detector holder movably coupled to a detector rail behind the shield, the flat panel image detector holder movably coupled to the detector rail to be manually moved vertically to position the detector holder at a vertical position based on the vertical position of the markers.

2. The stand of claim 1, wherein the markers identify multiple radiographic image areas of the total image area, the total image area being longer than a length of each image area, the desired total image area foamed by connecting a plurality of images of the plurality of image areas.

3. The stand of claim 1, wherein the shield structure includes a handle to be manually griped by a user to vertically move the shield structure along the vertical stand rail, to locate the shield at a desired shield height that positions the markers at vertical borders of the image areas.

4. The stand of claim 1, further comprising:
   a patient standing location in front of the shield for positioning a patient to image the desired total image area of the patient using the stand,
   wherein the shield is positioned between the patient and the vertical stand rail.

5. The stand of claim 4, wherein the stand includes:
   a base below and attached to the vertical stand rail, the base having arms with the wheels for rolling on a floor; wherein the patient standing location is between the arms of the base, and wherein the shield further comprises stitching markers including a substance with a large radiation attenuation coefficient, the stitching markers at locations used for connecting vertically adjacent images of vertically adjacent image areas of the desired total radiographic image area of the patient.

6. The stand of claim 1, wherein the shield structure is slidingly mounted on the vertical stand rail to allow the shield structure to move to a position, based on the height of the anatomy the patient, the position and area of vertically adjacent images, and a number of desired vertically adjacent images.

7. The stand of claim 1, wherein the markers are located at boundaries of the vertically adjacent image areas of the desired total image area of the patient, and wherein the detector holder includes holder rails that adjust in position to hold various sized detectors or to hold detectors at different orientations.

8. The stand of claim 1, wherein the markers are arranged at vertical levels at borders between vertically adjacent image areas, each image area comprising a maximum imagable area of the imager, and further including pointer markers at a same height as the markers, the pointer markers disposed on a back of the shield or on outer side edges of the shield to assist a user in vertically locating the detector holder at a correct vertical position based on the pointer markers for aligning an image detector to correct positions for image capture areas.

9. The stand of claim 1, wherein the shield column is slidingly mounted on the vertical stand rail to allow the height of the shield structure to be independently adjusted for the height of the anatomy of the patient with respect to the detector holder; and one of (1) the makers positioned on the shield at fixed height positions with respect to each other, or (2) mechanical detent positions along the detector rail, to demarcate a plurality of different imaging positions of a detector in the detector holder, that are desired to be imaged by a user to form the desired total radiographic image area.

10. A system for positioning a patient to image a total desired radiographic image area of the patient, the system providing multiple images of multiple image areas of the total image area, the system comprising:
a movable positioning stand comprising:
a stand frame having a vertical stand rail and wheels for moving the stand frame across a floor;
a shield structure having a shield column movably coupled to the vertical stand rail to be manually moved vertically along the vertical stand rail, the shield structure having arms or frame structure to hold a shield having a radio transparent material, the shield having markers including a substance with a large radiation attenuation coefficient, the shield column being movably coupled to the rails to be manually moved to position the shield at a shield height position, based on a height of anatomy of the patient desired to be imaged, the shield height position selected so that the markers provide marks for aligning an image detector to correct positions for imaging vertically adjacent and partially overlapping images of vertically adjacent image areas of a desired total image area of the patient;
a flat panel image detector holder movably coupled to a detector rail behind the shield, the flat panel image detector holder movably coupled to the detector rail to be manually moved vertically to position the detector holder at a vertical position based on the vertical position of the markers; and
a detector in the detector holder, the detector to receive radiation emitted by a radiation imaging source in front of the stand and the patient.

11. The system of claim 10, wherein the shield further comprises:
removable imagable markers to be manually located on the shield based on patient width and planned image positions of a desired total image, the removable markers to be detected by a control computer or manually by a user, the computer for connecting vertically adjacent images of image areas based on the markers.

12. The system of claim 11, wherein the source of radiation is positioned at a vertical height that is a same height as a center height of the desired total image area.

13. The system of claim 11, wherein the markers are at vertical borders of multiple radiographic image areas of the desired total image area, the desired total image area being longer than a length of each image area, the desired total image area formed by connecting a plurality of images of a plurality of image areas.

14. A method of using a portable positioning stand to position a patient and to locate a radiographic detector at multiple positions to create multiple images of multiple image areas identified by markers of a shield of the portable positioning stand, the method comprising:
locating the portable positioning stand to be radiated by a source of radiation; then
locating the patient in front of the stand; then
manually vertically aligning a shield of the stand to a shield height using a first movement and based on a height of anatomy of a patient desired to be imaged for a desired total image area and a vertical position of markers on the shield so that the markers identify a first and second image area of the desired total image area; and then
manually vertically aligning a detector of the stand to a first detector height position using a different second movement based the vertical position of the markers to image the first image area.

15. The method of claim 14, further comprising:
angling a radiation source to the first detector height position to radiate the first image area; then
irradiating a patient and the first image area to create a first image including the first image area at the first detector height position; then
aligning the detector of the stand to a second detector height position using a different third movement and based on the vertical position of the markers to image the second image area; then
angling the radiation source to the second detector height position to radiate the second image area; and then
irradiating the patient and the second image area to create a second image including the second image area at the second detector height position.

16. The method of claim 15, further comprising vertically centering a height of the radiation source to a height of a vertical center of the total desired image area within a shield's range of capture area.

17. The method of claim 15, wherein the markers are imaged in the first and second images; and further comprising:
vertically aligning the markers in the first and second images to form a desired total image including the desired total image area.

18. The method of claim 17, further comprising:
aligning the detector of the stand to a third detector height position using a different fourth movement and based on a vertical position of second markers to image a third image area; then
angling the radiation source to the third detector height position to radiate the third image area; then irradiating the patient and the third image area to create a third image including the third image area at the third detector height position, wherein the second markers are imaged in the second and third images; and then vertically aligning the second markers in the second and third images to form the desired total image including the desired total image area.

19. The method of claim 14, wherein vertically aligning the detector to the first and second detector height comprises manually vertically aligning the detector to demarcate accurate alignment locations for the detector to each image area using one of: (1) marker pointer positions that are visible from the front, side or back of the shield, or (2) mechanical detent positions along the detector rail.

20. The method of claim 14, wherein manually vertically aligning the shield comprises:

aligning based on vertical positions of three sets of the markers, locating a range of height of the anatomy within a range of height of a desired number of image areas within the vertical positions of the three sets of markers, and aligning based on the desired number of image areas.

21. The method of claim 14, wherein manually vertically aligning the shield includes:

locating a range of height of the anatomy within a range of height of a desired number of image areas within vertical positions of three sets of markers;

independently adjusting a height of the shield with respect to a height of the detector holder, wherein the makers are positioned on the shield at fixed height positions with respect to each other to demarcate a plurality of different imaging positions of a detector in the detector holder that are desired to be imaged by a user, and further comprising:

adjusting a height of the detector holder based on a height of the markers, after aligning the shield.

22. The method of claim 14, wherein aligning the shield includes manually locating removable imagable markers on the shield based on a patient width and planned image positions of a desired total image.

* * * * *